(12) United States Patent
Huard et al.

(10) Patent No.: US 8,609,821 B2
(45) Date of Patent: Dec. 17, 2013

(54) ANTIBODIES AGAINST APRIL AS BIOMARKERS FOR EARLY PROGNOSIS OF LYMPHOMA PATIENTS

(75) Inventors: Bertrand Huard, Juvigny (FR); Lars French, Zurich (CH); Olivier Donze, Vesenaz (CH); Maximilien Murone, Epalinges (CH)

(73) Assignee: Enzo Therapeutics, Inc., Farmingdale, NY (US)

( * ) Notice: Subject to any disclaimer, the term of this patent is extended or adjusted under 35 U.S.C. 154(b) by 921 days.

(21) Appl. No.: 12/452,937

(22) PCT Filed: Sep. 22, 2006

(86) PCT No.: PCT/EP2006/066625
§ 371 (c)(1),
(2), (4) Date: Feb. 17, 2011

(87) PCT Pub. No.: WO2007/039489
PCT Pub. Date: Apr. 12, 2007

(65) Prior Publication Data
US 2011/0143367 A1 Jun. 16, 2011

(30) Foreign Application Priority Data
Sep. 26, 2005 (EP) .................................... 05020881

(51) Int. Cl.
*C07K 16/00* (2006.01)

(52) U.S. Cl.
USPC ..................... 530/388.1; 435/7.1; 435/7.23

(58) Field of Classification Search
None
See application file for complete search history.

(56) References Cited

FOREIGN PATENT DOCUMENTS

| WO | WO 99/12965 | 3/1999 |
|----|-------------|--------|
| WO | WO 02/094192 | 11/2002 |

OTHER PUBLICATIONS

Ch'en, et al. (Jul. 2005) Cellular Immunology 236(1-2): 78-85.
Hahne, et al. (Sep. 1998) Journal of Experimental Medicine 188(6): 1185-1190.
López-Fraga, et al. (Oct. 2001) EMBO Reports 2(10): 945-951.
Ng, et al. (May 2005) Molecular Immunology 42(7): 763-772.

*Primary Examiner* — Mark Halvorson
(74) *Attorney, Agent, or Firm* — Anna D. DiGabriele Petti, Esq.

(57) ABSTRACT

The invention relates to antibodies directed against APRIL (A Proliferation Inducing TNF Ligand, also known as TALL-2), in particular the monoclonal antibody Aprily-2, hybridoma cells producing monoclonal antibody Aprily-2, and the use of a combination of an antibody against membrane-anchored APRIL and Aprily-2 in the diagnosis of B cell lymphoma resistance to treatment and the prognosis of clinical development of Diffuse Large B-Cell (DLBCL) lymphoma from high risk patients (>60 years and International Prognostic Index >2). An amino acid sequence GTGGPSQNGEGYP called Stalk, useful in the preparation of antibodies, is described.

6 Claims, 4 Drawing Sheets

SEQUENCE LISTING

```
<160> NUMBER OF SEQ ID NOS: 9

<210> SEQ ID NO 1
<211> LENGTH: 13
<212> TYPE: PRT
<213> ORGANISM: homo sapiens

<400> SEQUENCE: 1

Gly Thr Gly Gly Pro Ser Gln Asn Gly Glu Gly Tyr Pro
1               5                   10

<210> SEQ ID NO 2
<211> LENGTH: 20
<212> TYPE: DNA
<213> ORGANISM: Artificial Sequence
<220> FEATURE:
<223> OTHER INFORMATION: Primer for hTACI

<400> SEQUENCE: 2
ctgggtacct gcatgtcctg                                              20

<210> SEQ ID NO 3
<211> LENGTH: 20
<212> TYPE: DNA
<213> ORGANISM: Artificial Sequence
<220> FEATURE:
```

<223> OTHER INFORMATION: Primer for hTACI

<400> SEQUENCE: 3
agacttggcc ggactttgac                                           20

<210> SEQ ID NO 4
<211> LENGTH: 18
<212> TYPE: DNA
<213> ORGANISM: Artificial Sequence
<220> FEATURE:
<223> OTHER INFORMATION: Primer for hBCMA

<400> SEQUENCE: 4
gggcagtgct cccaaaat                                             18

<210> SEQ ID NO 5
<211> LENGTH: 20
<212> TYPE: DNA
<213> ORGANISM: Artificial Sequence
<220> FEATURE:
<223> OTHER INFORMATION: Primer for hBCMA

<400> SEQUENCE: 5
tcgttttcgt ggtgacaaga                                           20

<210> SEQ ID NO 6
<211> LENGTH: 20
<212> TYPE: DNA
<213> ORGANISM: Artificial Sequence
<220> FEATURE:
<223> OTHER INFORMATION: Primer for hAPRIL

<400> SEQUENCE: 6
atgccagcct catctccttt                                           20

<210> SEQ ID NO 7
<211> LENGTH: 20
<212> TYPE: DNA
<213> ORGANISM: Artificial Sequence
<220> FEATURE:
<223> OTHER INFORMATION: Primer for hAPRIL

<400> SEQUENCE: 7
tcctggattc ggacaccata                                           20

<210> SEQ ID NO 8
<211> LENGTH: 23
<212> TYPE: DNA
<213> ORGANISM: Artificial Sequence
<220> FEATURE:
<223> OTHER INFORMATION: Forward actin primer

<400> SEQUENCE: 8
ttaacgagaa gctgtgctac gtc                                       23

<210> SEQ ID NO 9
<211> LENGTH: 26
<212> TYPE: DNA
<213> ORGANISM: Artificial Sequence
<220> FEATURE:
<223> OTHER INFORMATION: Reverse actin primer

<400> SEQUENCE: 9
atagtcctgc ttgcttgctg atccac                                    26

ANTIBODIES AGAINST APRIL AS BIOMARKERS FOR EARLY PROGNOSIS OF LYMPHOMA PATIENTS

CROSS-REFERENCE TO RELATED APPLICATIONS

This application is the U.S. National Stage filing of International Application No. PCT/EP2006/066625, filed Sept. 22, 2006, which claims priority to EP 05020881.8, filed Sept. 26, 2005, the disclosures of each of which are hereby incorporated by reference.

FIELD OF THE INVENTION

The invention relates to antibodies directed against APRIL (also known as TALL-2), hybridoma cells producing monoclonal antibodies against APRIL, and the use of such antibodies in diagnosis of B cell lymphoma aggressiveness and the prognosis of clinical development of Diffuse Large B Cell (DLBCL) lymphoma in high risk patients.

BACKGROUND OF THE INVENTION

APRIL (A PRoliferation Inducing TNF Ligand, also known as TALL-2) and BAFF (also known as BLys, TALL-1) are closely related ligands of the TNF superfamily. They share two receptors, BCMA and TACI, whereas BAFF binds to a third receptor BAFF-R (also known as BR3) (Kalled, S. L., Ambrose, C. & Hsu, Y. M., *Curr Dir Autoimmun* 8, 206-42, 2005). BAFF-R, TACI and BCMA are predominantly expressed on B cells, in line with the role of these two TNF-ligands in humoral immune responses. The BAFF/BAFF-R pathway is crucial for maturation of peripheral B cells, and participates also in humoral responses by providing B cell co-stimulation and inducing Ig switch. APRIL has no obvious role in B cell development, but, like BAFF, is involved in humoral responses (Castigli, E. et al., *Proc Natl Acad Sci USA* 101, 3903-8, 2004). Dysregulation of the BAFF/APRIL pathways has been associated with several autoimmune diseases (Mackay, F., Sierro, F., Grey, S. T. & Gordon, T. P., *Curr Dir Autoimmun* 8, 243-65, 2005).

In addition to a role in autoimmune pathologies, APRIL and BAFF are implicated in the development of tumors (Mackay, F. & Tangye, S. G., *Curr Opin Pharmacol* 4, 347-54, 2004). In animal models, APRIL and BAFF over-expression induces development of B cell neoplasia. The involvement of these two TNF ligands in B cell tumors has been substantiated with human cell lines. Non-Hodgkin Lymphoma (NHL) and Multiple Myeloma (MM) cell lines were reported to aberrantly express these two TNF ligands, conferring an in vitro survival/proliferative advantage. In patients, the aberrant expression of BAFF and APRIL was confirmed by an elevated seric concentration.

Recently, APRIL binding to the sulfated glycosaminoglycan side chains of proteoglycans was demonstrated (Ingold, K. et al., *J Exp Med* 201, 1375-83, 2005). In contrast, BAFF does not bind proteoglycans, raising questions on the role of proteoglycans in APRIL function.

SUMMARY OF THE INVENTION

The invention relates to a monoclonal antibody Aprily-2 directed against soluble APRIL, and to hybridoma cells producing Aprily-2. Furthermore, the invention relates to the use of a combination of monoclonal antibody Aprily-2 and of monoclonal or polyclonal antibodies directed against a membrane-anchored APRIL fragment in the diagnosis of B cell lymphoma resistance to treatment and the prognosis of clinical development of Diffuse Large B Cell (DLBCL) lymphoma in high risk patients, in particular to the use of a combination of Aprily-2 and one antibody against the stalk domain of APRIL, and to the corresponding method of diagnosis and kits containing such antibodies. Furthermore, the invention relates to an amino acid sequence of the stalk domain of APRIL useful for preparing antibodies.

DETAILED DESCRIPTION OF THE INVENTION

The invention relates to the monoclonal antibody Aprily-2 directed against soluble APRIL, and to hybridoma cells producing this monoclonal antibody.

Monoclonal antibodies directed against soluble APRIL are obtained by immunizing mice with recombinant human APRIL (92-233) obtained by expression in E. coli. Hybridoma cells are prepared as described under standard conditions. The hybridoma cell line Aprily-2 producing monoclonal antibodies (mAb) Aprily-2 to soluble APRIL in concentrations of 80 µg/ml was deposited under the terms of the Budapest Treaty with the Collection Nationale de Culture des Microorganismes (CNCM), Institut Pasteur, 25, rue du Docteur Roux, F-75724 Paris CEDEX 15, on 23 Sep. 2005, and assigned accession number CNM I-3500.

Monoclonal antibody Aprily-2 is able to localize secreted APRIL. A second antibody raised against a defined APRIL sequence called the Stalk (GTGGPSQNGEGYP, SEQ ID NO:1) allows the reliable identification of cells producing APRIL in vitro in human tissues. This sequence (SEQ ID NO:1) is also an object of the invention.

Figure 1:
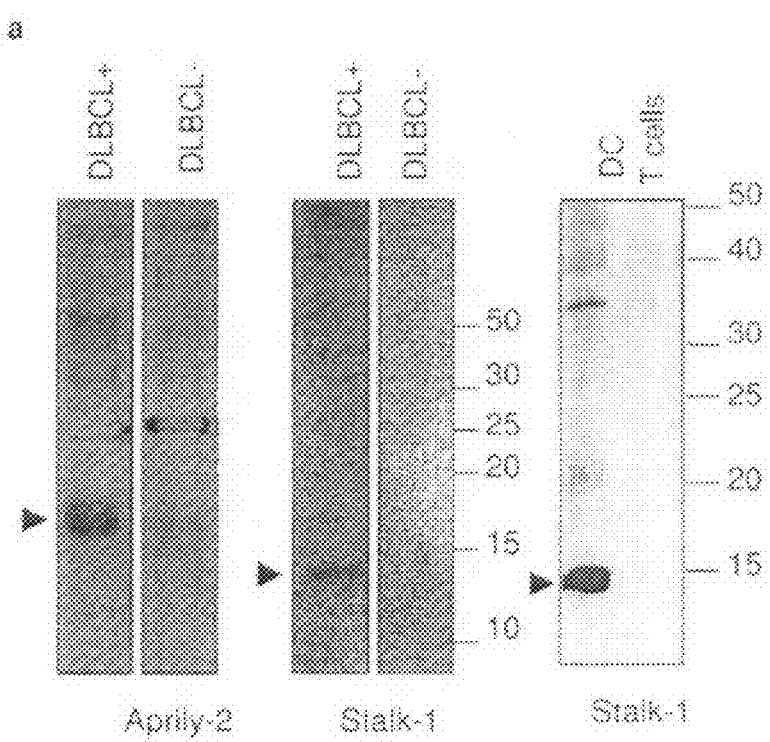
FIG. 1: Characterization of anti-APRIL antibodies identifying secreted APRIL and cell producing APRIL
(a) Extracts (20 µg) from IHC-positive and negative DLBCL tissue samples were analyzed by Western-blot with Aprily-2 (2 µg/ml) and Stalk-1 (5 µg/ml). A 18 kDa band corresponding to secreted APRIL was revealed with Aprily-2 (left panel), while Stalk-1 identified a 14 kDa band (middle panel). Similar 14 kDa reactivity was observed with Stalk-1 on DC lysates (20 µg) (right panel). The reactivity is representative of three IHC-positive and two IHC-negative tumor lysates.
(b) Western blot specificity was ascertained in blocking experiments. Aprily-2 was pre-incubated with 10 µg/ml of acrpAPRIL (APRIL [88-233] fused to ACRP30 [16-108]) or acrpCTRL. Stalk-1 was pre-incubated with 10 µg/ml of the stalk peptide or an irrelevant peptide, prior to Western blot analysis.
Figure 1:
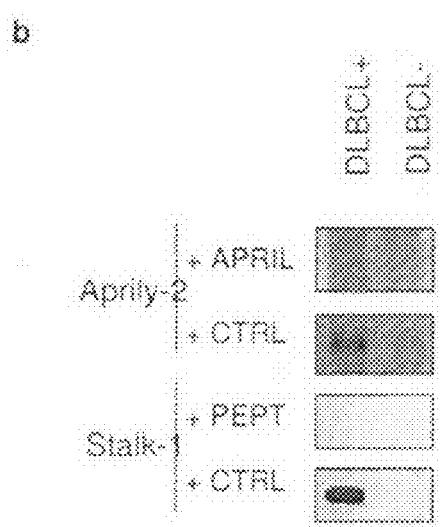

None of the antibodies against APRIL generated up to date are capable of identifying cells producing APRIL due to the early cleavage of newly synthesized APRIL. The stability in APRIL producing cells of a particular fragment of APRIL, called the Stalk, which remains associated with the cells after APRIL processing, is important. Indeed, this is the major APRIL product detectable in cells producing APRIL (FIG. 1a). Any antibody directed against the sequence GTGGPSQNGEGYP (SEQ ID NO:1) of human APRIL (e.g. the polyclonal antibody Stalk-1) is able to identify this 15 kDa Stalk fragment.

With such a combination of antibodies, i.e. the monoclonal antibody Aprily-2 and any (monoclonal or polyclonal) antibody directed against the Stalk fragment, APRIL can be easily detected. Such a method is a further aspect of the invention. It is observed that APRIL is strongly expressed in about half of the high-grade B cell lymphomas, such as DLBCL. The other half did not show any up-regulation compared to healthy tissues. In DLBCL lesions showing strong APRIL up-regulation, detailed analysis revealed that APRIL is mainly produced by infiltrating neutrophils (in rare cases by histiocytes), whereas secreted APRIL is concentrated on tumor cells. The role of APRIL in the DLBCL lesions was studied in vivo with a retrospective study of patients harboring different level of APRIL expression. A strong correlation between high expression of APRIL in tumoral lesions and absence of response to conventional treatments in high clinical risk patients was observed, indicating a role for APRIL in human lymphoma aggressiveness (resistance to treatment). High clinical risk patients are defined as a patient over 60 years of age and/or with an international prognostic index (IPI)>2. The International Prognostic Index (IPI) was designed to further clarify lymphoma staging. The IPI predicts the risk of disease recurrence and overall survival by taking into account 4 factors such as i) general health (also known as performance status), ii) stage of tumor invasion (Ann Arbor staging), iii) the presence or absence of an elevated serum enzyme named lactate dehydrogenase (LDH) (correlates with tumor size), and iv) number of extranodal sites. Each stage when scored positive counts as 1 point; over 60 years of age and IPI >2 is associated with high risk patients (Wilder, R. B. et al., Cancer, 94, 3083-3088, 2002).

APRIL up-regulation in high grade B cell lymphoma strengthens tumor resistance to treatment and is likely to explain treatment failure for high clinical risk patients. The antibodies described, i.e. the combination of monoclonal antibody Apriliy-2 with a polyclonal or monoclonal antibody against the APRIL fragment called Stalk, constitute the first suitable pair to assess APRIL expression in patient tumor biopsy.

The antibody pair described above is useful to identify easily by immunohistochemistry, at the time of disease diagnosis, patients with important risk to fail to respond to current standard treatments. Such early diagnosis will help to identify patients eligible for more intensive treatments than currently applied. In addition to cost saving, such early diagnosis will help improving success in the treatment of high grade B cell lymphoma, i.e. the aggressive form of B cell lymphoma. The present invention relates to a method of diagnosis of an aggressive form of B cell lymphoma (resistance to treatment) wherein a B cell lymphoma biopsy specimen is analyzed for binding of monoclonal antibody Aprily-2 and of a polyclonal or monoclonal antibody against the stalk fragment of APRIL, and an aggressive form is diagnosed if the two antibodies bind to the specimen.

APRIL determination in tumor biopsy has also an important prognosis value for other B cell tumors, such as low-grade lymphomas, leukemias and multiple myelomas. In addition, it is useful for solid tumors, such as carcinomas and melanomas.

Identification of Antibodies Selectively Recognizing Secreted and Membrane-Associated APRIL To study in situ APRIL expression, APRIL-specific antibodies with different specificities are selected. The monoclonal antibody of the invention, Aprily-2, recognizes the C-terminal TNF homology domain of APRIL secreted upon furin cleavage. The polyclonal rabbit antiserum Stalk-1 recognizes the membrane-proximal sequence in APRIL extracellular domain. This domain, called stalk hereafter, stays associated to the cell membrane after furin cleavage. Selective stainings on APRIL-transfected cells, fixed and embedded into paraffin, are obtained with these antibodies, indicating specificity for immunohistochemical use.

Stalk-1 and Aprily-2 generate positive staining by immunohistochemistry (IHC). Results are collected in Tables 1, 2 and 3. The protein products detected by Stalk-1 and Aprily-2 in lysates from tumor biopsy were biochemically characterized. Western blot analysis shows that Aprily-2 identifies a predominant 18 kDa band, whereas Stalk-1 detects a 14 kDa band in IHC positive biopsy (FIG. 1a). No such bands are observed in IHC negative biopsy. The 18 kDa band recognized by Aprily-2 is compatible with the size of secreted APRIL. The 14 kDa band recognized by Stalk-1 is compatible with the predicted size of the APRIL stalk domain after cleavage and is also observed as a predominant band in DC lysates (FIG. 1a, right panel). In the latter experiment, full length APRIL (32 kDa) is not significantly detected, indicating that most of APRIL is rapidly cleaved and secreted after synthesis. Specificity is assessed in competition experiments. Addition of soluble acrpAPRIL or stalk peptide to the respective antibodies prior to Western blot analysis abolishes the recognition of the 18 kDa and 14 kDa bands respectively (FIG. 1b), demonstrating that these proteins express the relevant epitopes. The analysis indicates that the stalk of cleaved APRIL remains stable in APRIL-producing cells, making Stalk-1 a valuable tool to detect APRIL-producing cells. In contrast, Aprily-2 detects secreted APRIL.

Strong Up-regulation of APRIL in DLBCL Biopsy

Stalk-1 and Aprily-2 are used to stain multi-tumor arrays prepared from paraffin-embedded tissues of NHL and control healthy tonsils. Among these, 50% of DLBCL lesions were strongly positive for secreted APRIL (Aprily-2 staining). The remaining cases showed only focal staining of cells (Table 1). In contrast, tissues from Mucosa Associated Lymphoid Tissue (MALT), Follicular Cell (FCL), Mantle Cell (MCL), Marginal Zone lymphomas (MGZL), as well as nodular Chronic Lymphocytic Leukemia (CLL) harbored only a focal Aprily-2 staining. In non-tumoral lymphoid tissues, such as tonsils, focal Aprily-2 staining was observed. The same NHL arrays were stained with Stalk-1, and more than 95% of the cases positive for Aprily-2 were also stained with Stalk-1 (Table 1). Hence, in the detection of secreted APRIL correlates with the presence of APRIL-producing cells in tumor lesions. Taken together, this indicates that APRIL expression is markedly up-regulated in 50% of the DLBCL lesions.

TABLE 1

APRIL expression is strongly up-regulated in high-grade B cell lymphomas, hodgkin-like lymphoma and multiple myeloma Multiple B cell lymphoma arrays and healthy tissues were immunostained with Aprily-2 (2 µg/ml) or Stalk-1 (5 µg/ml) antibody. Numbers of cases with strong staining (high) or focal (low/negative) stainings are indicated.

|  | n |  | high | low/negative |
|---|---|---|---|---|
| NHL lesions, lymphoma |  |  |  |  |
| Diffuse Large B cell Lymphoma | 312 | Aprily-2 | 142 | 170 |
|  |  | Stalk-1 | 135 | 177 |
| Burkitt Lymphoma | 14 | Aprily-2 | 4 | 10 |
|  |  | Stalk-1 | 3 | 11 |
| Follicular Cell Lymphoma | 149 | Aprily-2 | 4 | 145 |
|  |  | Stalk-1 | 3 | 146 |
| Chronic Lymphocytic Leukemia | 34 | Aprily-2 | 1 | 33 |
|  |  | Stalk-1 | 1 | 33 |
| Mantle Cell Lymphoma | 27 | Aprily-2 | 1 | 26 |
|  |  | Stalk-1 | 1 | 26 |
| Marginal Zone Lymphoma | 6 | Aprily-2 | 0 | 6 |
|  |  | Stalk-1 | 0 | 6 |
| Hodgkin-like Lymphoma | 663 | Aprily-2 | 90 | 573 |
|  |  | Stalk-1 | 98 | 557 |
| Multiple Myeloma | 10 | Aprily-2 | 0 | 0 |
|  |  | Stalk-1 | 10 | 0 |
| Healthy tissues |  |  |  |  |
| Tonsils | 21 | Aprily-2 | 0 | 21 |
|  |  | Stalk-1 | 0 | 21 |

APRIL is strongly upregulated in diffuse large B cell lymphoma, Hodgkin-like lymphoma and multiple myeloma (Table 1), but also in some other carcinomas (Table 2) and skin cancers (Table 3).

TABLE 2

APRIL expression is strongly up-regulated in various carcinomas Carcinoma tissue arrays and healthy tissues were immunostained with Aprily-2 (2 µg/ml) or Stalk-1 (5 µg/ml) antibody. Positive staining (+) staining is indicated.

| Tissue | Carcinoma type | APRIL staining |
|---|---|---|
| bladder | urothelial | + |
|  | transitional | + |
| cervix | squamous | + |
| breast | adeno | + |
| prostate | adeno | + |
| kidney | oncocytoma | + |
|  | renal cell | + |
|  | papillary | + |
|  | chromophobe | + |
| ovary | serous | + |
|  | mucinous | + |
|  | endometriod | + |
| testis | seminoma | + |
|  | embryonal | + |

TABLE 3

APRIL expression is strongly up-regulated in various skin cancers Skin cancer biopsies (basal cell carcinoma and metastatic melanoma) and healthy tissues were immunostained with Aprily-2 (2 µg/ml) or Stalk-1 (5 µg/ml) antibody. Number of positive staining are indicated for 4 basal cell carcinomas and 8 metastatic melanomas.

| Skin cancer | Basal cell carcinomas | 4/4 |
|---|---|---|
|  | Metastatic melanomas | 6/8 |

For detailed analysis, Aprily-2 and Stalk-1 stainings were characterized on whole sections from DLBCL lesions. Aprily-2 revealed a patchy cell-surrounding staining, with some cells having a morphology compatible with tumor cells. A similar pattern was also observed with two other mononclonal antibodies to soluble APRIL (Aprily-6 and Aprily-8). In contrast, Stalk-1 revealed a cellular staining. Aprily-2 and Stalk-1 stainings were competed with acrpAPRIL and stalk peptide, respectively. None of the cells stained with Stalk-1 had a morphology compatible with tumor cells. The low or undetectable APRIL expression in 50% of the DLBCL patients was confirmed with whole section stainings for both Stalk-1 and Aprily-2. This experiment strongly suggests that the source of APRIL in tumoral lesions is not the tumor itself but rather the stroma. Once secreted, cleaved APRIL appears to dissociate from APRIL-producing cells.

Tumor-infiltrating Neutrophils Produce APRIL

APRIL-producing cells were precisely identified in situ. High magnification analysis of immunoperoxidase staining with Stalk-1 readily indicates that positive cells have a trilobular nucleus, highly characteristic of neutrophils. In addition, a few positively labeled cells with endothelial morphology are also observed in the sections. Neutrophil identity is confirmed by combining Stalk-1 staining with anti-CD15 and anti-elastase, both being common markers for neutrophils. In these sections, almost all anti-stalk positive cells are also stained with the neutrophil markers. The APRIL-producing neutrophils were localized in the lesions. Stalk-1 staining was combined with CD20 staining, used as a B-cell lymphoma marker. APRIL-producing cells are located close to the tumor foci. The tumor cells do not express APRIL, since no overlap is observed between the stalk-1 and CD20 stainings. Altogether, this indicates that neutrophils infiltrating the tissues invaded by DLBCL tumor cells are the major source of APRIL.

Neutrophils Producing APRIL are Recruited Upon Inflammation.

To further characterize APRIL expression, neutrophils from healthy volunteers were studied. Peripheral blood neutrophils isolated from healthy donors express APRIL mRNA and are stained with Stalk-1. By contrast, peripheral neutrophils are not stained with Aprily-2. This discrepancy between Aprily-2 and Stalk-1 stainings is not observed with 293T cells transfected with full length APRIL. This confirms that endogenous full length or cleaved APRIL is not detected in neutrophils, in contrast to transfected 293T cells. Neutrophils infiltrating non-tumoral inflamed tissues were also tested. Acute appendicitis, known to be highly infiltrated by neutrophils, contain abundant cells stained with Stalk-1. Upon higher magnification, the stained cells have the same morphology as Stalk-1 positive cells in DLBCL lesions. This indicates that mature circulating neutrophils constitutively express APRIL and that production of APRIL in inflammatory reactions, including DLBCL development, is ensured by recruited neutrophils.

Proteoglycans Impair APRIL Secretion

Figure 2:
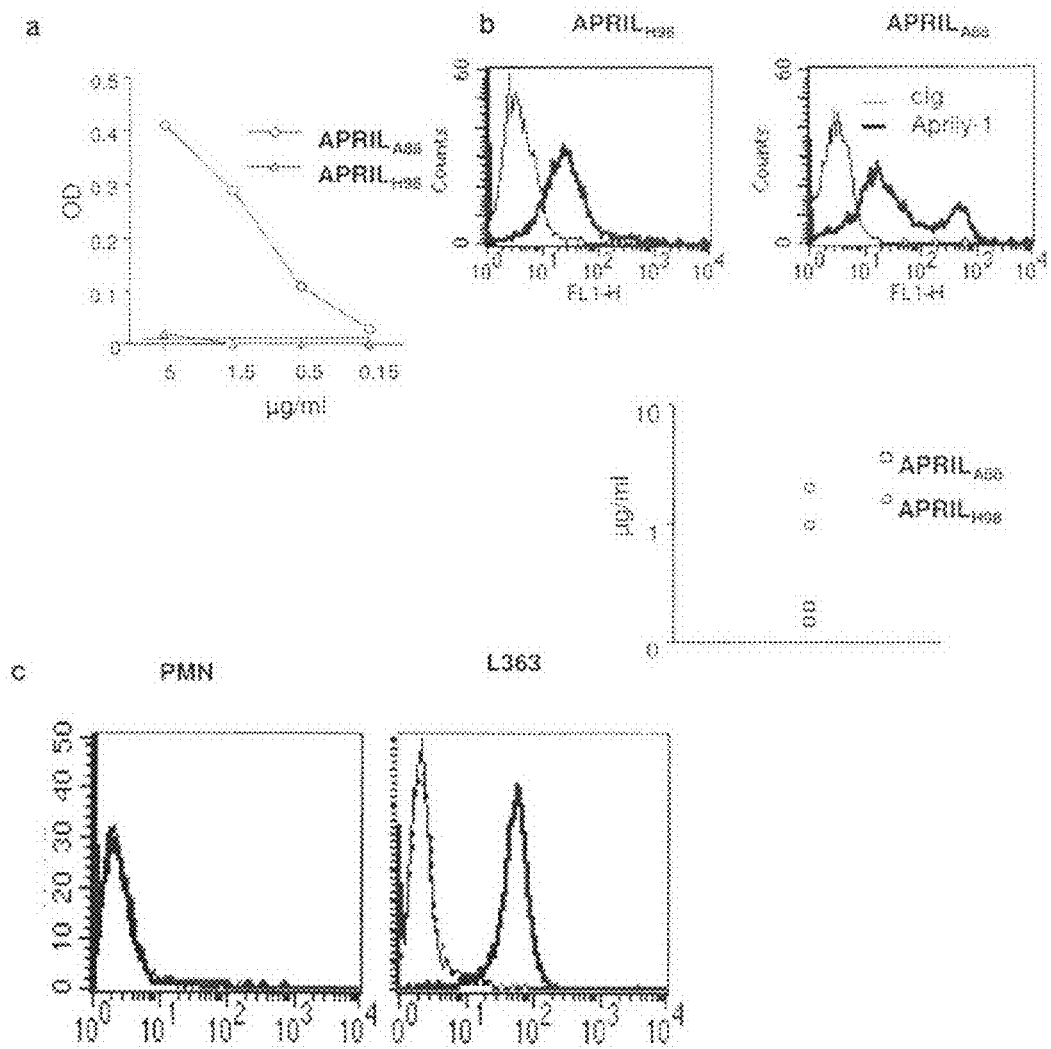
FIG. 2: Cellular proteoglycans impair APRIL secretion
(a) Binding of trimeric $APRIL_{A88}$ and $APRIL_{H98}$ to coated Heparan Sulfate Proteoglycans (HSPG) from mouse sarcoma (1 µg/ml) was revealed in ELISA with Aprily-9 (1 µg/ml).
(b) 293T cells were transfected with a plasmid encoding $APRIL_{A88}$ or $APRIL_{H98}$. Three days later, cells were harvested, fixed/permeabilized and stained with the Aprily-1. Fluorescence was analyzed by flow cytometry. Supernatants were collected and quantified in a sandwich ELISA with BCMA-Ig as capture and Aprily-5 as detection.
(c) Binding of $acrpAPRIL_{A88}$ was assessed on PMN isolated from a healthy donor and analyzed by flow cytometry. Acrp30 was used as negative control (CTRL). The binding of $acrpAPRIL_{A88}$ in the presence or absence of heparin [H] (1/100) on L363 is shown as positive control.
Aprily-1, Aprily-5 and Aprily-9 are monoclonal antibodies to soluble APRIL related to Aprily-2.

It has previously been shown that APRIL interacts with cell surface proteoglycans. APRIL interaction with proteoglycans was confirmed in a cell-free ELISA assay by using purified heparan sulfate proteoglycan (HSPG) from a mouse sarcoma for capture and Aprily-9 for detection. In this case, recombinant $APRIL_{A88}$ but not recombinant $APRIL_{H98}$, lacking the proteoglycan-binding site, bind to coated proteoglycans (FIG. 2a). This interaction of huAPRIL with heparan sulfate side chains of murine proteoglycans indicates that APRIL is likely to interact with a wide range of heparan sulfate proteoglycans, no matter what the proteic core is. In addition, it indicates that no other cellular proteins are required for the interaction. The influence of proteoglycans on the secretion of APRIL was assessed. 293T cells, known to express proteoglycans, were transfected with a plasmid encoding $APRIL_{A88}$ or $APRIL_{H98}$. FIG. 2b shows that some 293T-transfected cells retain high levels of $APRIL_{A88}$, while there were only modest levels of cell retention with $APRIL_{H98}$. The cell retention is confirmed by quantification of secreted APRIL in the supernatant. 293T cells transfected with $APRIL_{H98}$ secrete about 2-3 µg/ml of the recombinant protein, while ten fold less secretion is achieved with $APRIL_{A88}$ (FIG. 2b). It was tested whether neutrophils producing APRIL express proteoglycans. Binding of $APRIL_{A88}$ to the cell surface assesses proteoglycan expression. FIG. 2c shows that peripheral neutrophils do not bind APRIL. In contrast, the L363 cell line (Multiple Myeloma cells expressing syndecan-1) binds APRIL and this binding is completely inhibited by heparin. This shows that peripheral neutrophils are devoid of any detectable proteoglycans able to bind APRIL. The deficit in APRIL-binding proteoglycan expression by neutrophils renders them fully competent to secrete APRIL.

Proteoglycans Concentrate Secreted APRIL Close to DLBCL Cells in Tumor Lesions

Proteoglycan expression in DLBCL lesions was assessed. Syndecan-1 is not expressed. In contrast, expression of syndecan-4 is observed in half of the cases analyzed (n=6). Secreted APRIL is located at syndecan-4 expression sites in the tumor lesion. The Aprily-2 staining is always located at site of syndecan-4 expression with a perfect overlap, strongly suggesting a tight interaction of APRIL with syndecan-4 in situ. The fact that some syndecan-4 is free indicates either that APRIL is not produced in saturating quantity, or that it is consumed in the tumor lesions, while proteoglycans are not. To identify the cells expressing syndecan-4, CD20 and syndecan-4 staining was combined. DLBCL tumor cells homogeneously express syndecan-4. The Syndecan-4 staining constitutes an inner ring compared to the membranous CD20 staining, probably reflecting an intracellular localization of syndecan-4. Syndecan-4 expression is also observed in tissues surrounding the tumor bed and devoid of any tumor cells. Aprily-2 staining was combined with CD20 staining. Secreted APRIL is concentrated close to the tumor, some being directly associated to tumor cells and some being associated to non-tumoral cells. The latter most likely corresponds to the non-tumor cells expressing syndecan-4. These cells are always localized at the tumor periphery and are absent from tissue sections not invaded by tumor cells. Furthermore, secreted APRIL concentrates mainly at the tumor periphery and is absent in the deep tumor bed. APRIL binding to tumor cells can be confirmed at high magnification with an Aprily-2 immunoperoxidase staining. Taken together, this analysis shows that APRIL, once secreted by neutrophils, accumulates at the tumor periphery bound to tumor and tissue proteoglycans.

DLBCL Tumor Cells Express BCMA and Proteoglycan Co-Receptors for APRIL

Figure 3:
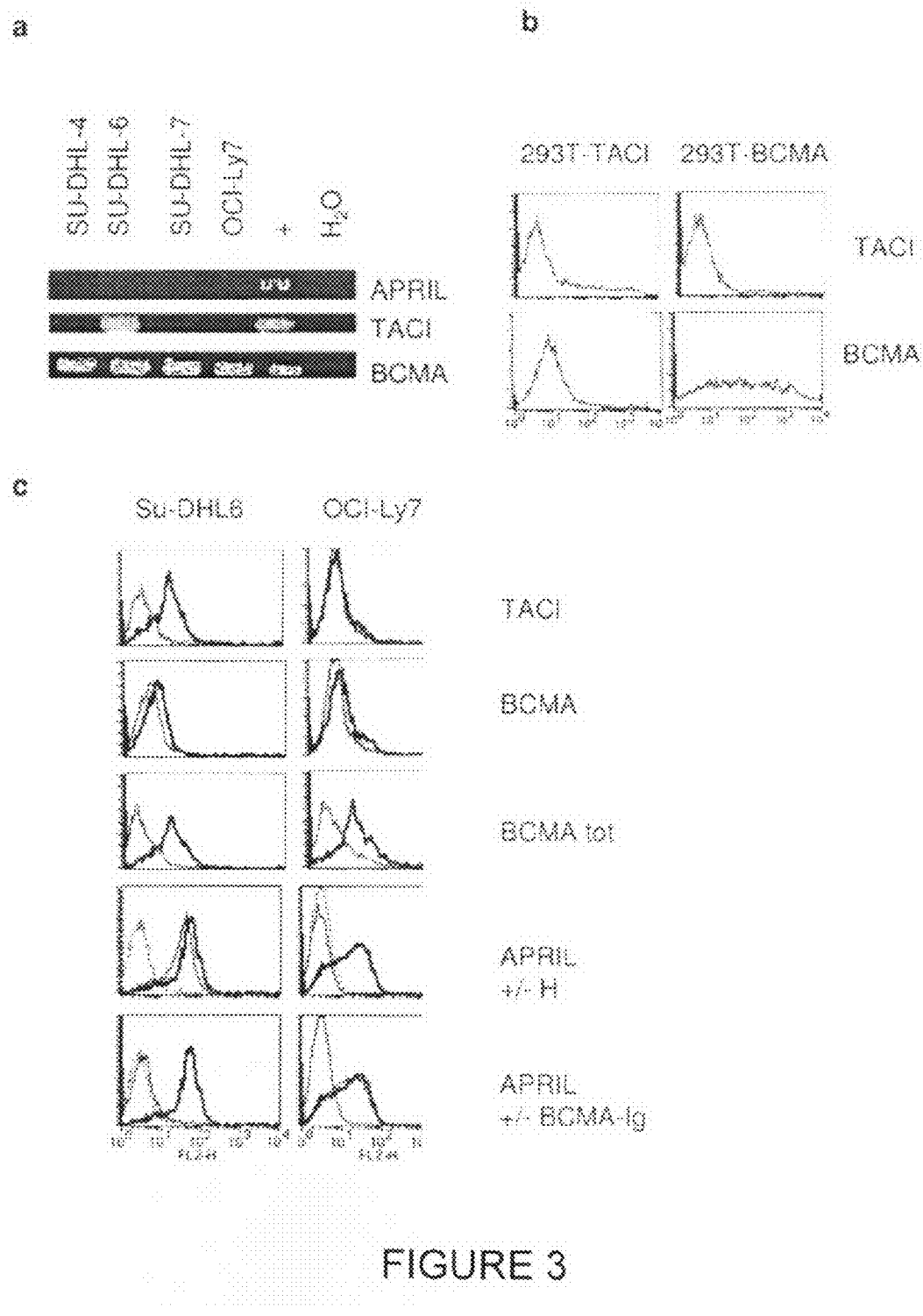
FIG. 3: DLBCL tumor cells express BCMA and proteoglycan co-receptor
(a) TACI, BCMA and APRIL mRNA expression in DLBCL lines was analyzed by RT-PCR (40 cycles). Positive controls (+) were peripheral CD19[+] B cells for TACI and BCMA, and DC for APRIL. $H_2O$ was used as negative control.
(b) Specificity of the anti-TACI and BCMA mAb (monoclonal antibody) is shown on transfected 293T cells.
(c) Flow cytometry analysis of APRIL-R expression on DLBCL lines was performed with the indicated reagents. Surface expressions on intact cells are shown. For BCMA, total expression after cell permeabilization is also shown. Control stainings (IgG1 isotype control) are shown as dotted lines.
Data obtained with binding of acrpAPRIL are shown as thick lines and thin lines when pre-incubated with heparin [H] (1/100) or BCMA-Ig (50 pg/ml) (thin lines). Control stainings (acrpCTRL) are shown as dotted lines. SU-DHL-4 and -7 harbored identical staining to OCI-Ly7.

APRIL receptor expression was investigated in DLBCL lesions. No antibodies are available to date to detect endogenous BCMA or TACI on formaldehyde-fixed tissues. DLBL cell lines established from patients were therefore used. Messenger RNA expression analysis by RT-PCR shows expression of BCMA in all the cell lines tested, while only one, SU-DHL 6, expresses TACI (FIG. 3a). In this RT-PCR analysis, the absence of APRIL expression in DLBCL cell lines is confirmed. Anti-TACI and BCMA mAbs are used to detect protein expression. Specificity of the anti-TACI, and BCMA mAbs is validated on transfected-293T cells (FIG. 3b). TACI protein expression is detected in SU-DHL-6, while it is not observed in OCI-Ly7 (FIG. 3c) and SU-DHL-4 and -7. The anti-TACI 1A1 mAb binds to the second cystein-rich domain of TACI, confirming the absence of TACI protein in these DLBL cell lines. Expression of surface BCMA is barely detectable on the DLBCL, but significant BCMA staining is always observed after cell permeabilization. APRIL binding was assessed with acrpAPRIL, containing the proteoglycan-binding site. acrpAPRIL binds homogenously to all DLBCL cell lines (FIG. 3c). However, when inhibition with heparin is assessed, complete inhibition is observed on OCI-Ly7 but no inhibition is found on SU-DHL6. In addition, BCMA-Ig inhibits binding on SU-DHL6 but not on OCI-Ly7. This indicates that SU-DHL6 expresses TACI as surface receptor for APRIL without proteoglycans, while OCI-Ly7 expresses surface proteoglycans without TACI. For BCMA, the expression is homogeneously expressed in DLBCL lines with a major intracellular pool. Altogether, this indicates heterogeneity in APRIL-R expression among DLBCL lines. The majority of DLBCL tumor cells expresses BCMA and proteoglycan co-receptors.

High APRIL Expression in Tumor Lesions of DLBCL Patients is Associated with Reduced Survival Rate.

Figure 4:
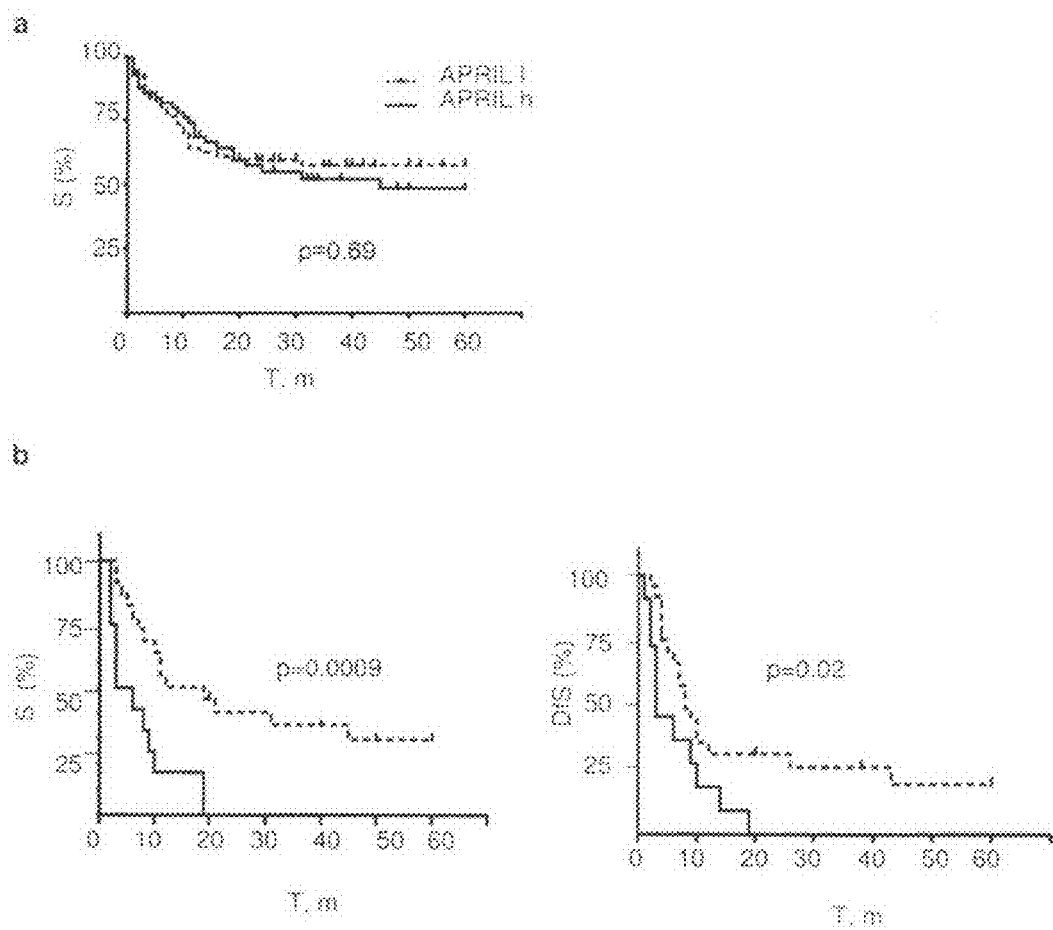
FIG. 4: High APRIL expression in DLBCL patients is associated with decreased survival Survival was retrospectively studied in patients stratified according to APRIL expression.
(a) All patients. dotted line: low APRIL, normal line: high APRIL. S=overall survival, time (T) in months (m).
(b) High-risk patients, >60 years and IPI>2. dotted line: low APRIL, normal line: high APRIL. S=overall survival, DfS=disease-free survival, time (T) in months (m).

The role of APRIL in DLBCL was assessed by a retrospective clinical analysis of 233 patients analyzed for APRIL expression in biopsy samples. The disease stage, level of circulating LDH, in situ proliferation index, DLBCL types and age were first determined when data were available. There were no significant differences between "high" and "low APRIL expressors" in terms of stage, LDH level, tumor proliferation index, and age. In addition, low and high level of APRIL expression was observed in the two DLBCL subtypes, germinal center and activated, indicating no obvious correlation between levels of APRIL expression and standard clinical parameters at the time of diagnosis. The survival rate and the time to relapse following CHOP (cyclophosphamide, doxorubicin, vincristin and prednisolone) treatment was then analyzed. From the 233 patients analyzed for APRIL expression, 100 had trackable clinical data. Interestingly, for the high risk patients (>60 years and IPI>2), a dramatic decrease (p=0.0009) in survival measured by the absence of response to treatment was observed in the "high APRIL expressor" group (FIG. 4 b). Moreover, for the same population of patient (>60 years/IPI>2 and APRIL high), the disease-free period was much shorter than that for the APRIL low population (p=0.02) (FIG. 4 b). These observations strongly suggest that APRIL has a tumor-promoting role in DLBCL.

Discussion of the Experimental Results

APRIL up-regulation is observed in about 50% of DLBCL cases. The main source of APRIL in positive samples are neutrophils. No evidence for APRIL expression by tumor cells was found. APRIL production by tumor cells, if occurring, is extremely low in situ, compared to tumor-infiltrating neutrophils. A low production of APRIL by DLBCL cells is not contradictory with the results obtained with cell lines, since it could very well explain the survival effect observed on these DLBCL cell lines when APRIL is added exogenously. In situ expression of APRIL by tumor-infiltrating neutrophils is consistent with the in vitro expression confined to cells of the myeloid lineage. However, it indicates that APRIL is selectively produced in situ by neutrophils, and not by other cells from the myeloid lineage, such as monocytes/macrophages also infiltrating DLBCL. This host-derived production of APRIL in B-cell lymphomas is likely to explain the selective up-regulation in DLBCL lesions, since such lymphomas are classified as high-grade, developing with a more pronounced host cell infiltration, compared to other B cell lymphoma/leukemia (MALT, CLL, FCL, MCL, MGZL), classified as low-grade lymphomas. In these latter B-cell tumors, APRIL expression levels are comparable to that found in inflamed non-tumor invaded tonsils.

Secreted APRIL was found associated to tumor cells. This localization was ensured by HSPG binding APRIL. In some cases, tumor-expressed HSPG was identified as Syndecan-4. In the other DLBCL cases, Syndecan-4 was not expressed, but the Aprily-2 staining observed was identical, with characteristic punctuation, indicative of an association with another HSPG. The punctuated APRIL/HSPG staining very much likely reflects proteoglycan clustering induced upon ligand binding In the tissues invaded by tumor cells, proteoglycans serve to concentrate this ligand secreted by infiltrating neutrophils close to receptor-expressing tumor cells. To maximize the efficiency of the process, APRIL-producing neutrophils are devoid of proteoglycans. It is possible that proteoglycan co-receptor function could be mediated in cis by tumor cell-expressed proteoglycans and in trans by proteoglycans expressed on cells surrounding the tumor.

APRIL co-stimulation in B cells can be performed either by triggering BCMA, TACI, or both. TACI is not constantly expressed on DLBCL tumoral cells. BCMA is uniformly expressed in the DLBCL cell lines tested. Uniform BCMA expression strongly suggests that BCMA serves to transmit an APRIL co-stimulatory signal. BCMA staining is low on intact DLBCL tumor cells, but significantly enhanced after permeabilization, consistent with the presence of an intracellular pool of BCMA, located in the golgi apparatus. In addition to BCMA, DLBCL tumoral cells express proteoglycans binding to APRIL. The low level of BCMA expression may indicate a dependency for a co-receptor, such as proteoglycans, concentrating APRIL at the cell surface.

High concentrations of a B-cell co-stimulatory molecule such as APRIL in B cell tumors provides a continuous survival/proliferative signal favoring tumor development and enhancing aggressiveness. For low risk patients (>60 years and IPI <2), the current efficacy achieved with treatments combining chemotherapy and Rituximab apparently does not allow detection of a role for APRIL. However, for high risk patients (>60 years and IPI>2), known to be less responsive to such treatments, high APRIL expression in tumor lesions is associated with strongly reduced survival rate. The fact that DLBCL cell lines and patient evolution after diagnosis are dependent on APRIL suggests a post-transformation role for this molecule in the tumorigenesis process. In high risk patients, APRIL is therefore a valuable prognosis tool in the tuning of treatment strength, and represents a valuable therapeutical target for subjects with high expression of APRIL in this group of patients.

Prognosis of Clinical Development of B Cell Lymphoma

Based on the experimental results explained hereinbefore, a combination of the monoclonal antibody Aprily-2 against soluble APRIL (quantifying secreted APRIL in the lesion) with a polyclonal or monoclonal antibody against the stalk fragment of membrane-anchored APRIL (SEQ ID NO:1), identifying cells producing APRIL, is useful in the diagnosis of B cell lymphoma aggressiveness (resistance to treatment). Particularly preferred is the use of a combination of Aprily-2 with the polyclonal antibody against membrane-anchored APRIL called Stalk-1.

In particular, the combination of the mentioned antibodies may be used to make a prognosis of the aggressiveness of a B cell lymphoma and to predict the likely clinical outcome. Such a prognosis is helpful in devising corresponding therapeutic treatment. Particularly useful is such a method in the prognosis of B cell lymphoma in high risk patients (IPI>2).

Kits Useful in the Diagnosis of B Cell Lymphoma.

The invention furthermore relates to kits comprising monoclonal antibody Aprily-2 and one polyclonal or monoclonal antibody against the stalk fragment of membrane-anchored APRIL, e.g. Stalk-1. The kit may contain further antibodies directed to other B cell lymphoma biomarkers, furthermore standard equipment, solutions and directions for use to perform the diagnostic tests, APRIL or APRIL fragments and control peptides as standards, and the like. Preferred is a corresponding kit comprising polyclonal antibody Stalk-1 and monoclonal antibody Aprily-2.

EXAMPLES

Antigen Preparation

Recombinant human APRIL (92-233) was produced in bacteria. Cells transformed with the APRIL expression vector were inoculated in 8 ml L broth (LB) with AK (ampicillin 100 µg/ml+kanamycin 50 µg/ml) and grown over night at 37° C. 8 ml of over night culture are diluted in 400 ml LB+AK and grown at 37° C. Isopropyl-β-D-1-thiogalactopyranoside (IPTG) is added at a 0.5 mM final concentration and cells are grown 6 h at 37° C. Bacteria are harvested, the pellet resuspended in phosphate buffered saline (PBS), and lysed in a french press. The cell lysate is transferred in 2 ml Eppendorf tubes and centrifuged 5 min. at 13'000 rpm at room temperature. The pellet containing recombinant human APRIL in inclusion bodies is resuspended in SDS (sodium dodecyl sulfate) Sample Buffer, sonicated, reduced and loaded on a SDS gel. The band corresponding to recombinant human APRIL is electroeluted.

Immunizations

Three mice were injected with 150 µg of recombinant human APRIL (92-233) each diluted in PBS and Complete Freund's adjuvant. Fourteen days later mice were boosted with the same amounts of antigen in Complete Freund's adjuvant. Twenty-eight days later mice were bled to assess their immune response to recombinant human APRIL (92-233) and an ELISA was performed with different dilutions of the serum. Mice with positive sera were boosted again with recombinant human APRIL (92-233) in PBS after forty-five days. Three days later the spleens were harvested.

Cell Fusion, Screening and Subcloning

Spleens were homogenized in a sterile glass-glass homogenizer in 10 ml of RPMI-1640 with 6-8 strokes using the borosilicated pestle. The suspension was transferred into a 50 ml Falcon tube, and cells spinned down at 300×g for 10 min at room temperature. Cells were re-suspended in 10 ml of RPMI-1640 medium and plasmocytes were counted. 10-20× $10^7$ spleen cells and 10-20×$10^6$ myeloma cell clones (P3-X63Ag8 or NSI) (ratio 10/1) were mixed for the fusion, and spinned. 0.5 ml of pre-warmed PEG 1500 was added to the pellet drop-wise along the tube wall, and the tube was kept for 3 min at 37° C. while shaking gently every minute. 5 ml of RPMI-1640 medium (pre-warmed at 37° C.) were added along the tube wall over a period of 10 min (0.5 ml/min), followed by a 1 min incubation at 37° C. 5 ml of RPMI-1640 medium were added again over a period of 5-6 minutes. Cells were pelleted by centrifugation for 10 min, 300×g, at room temperature, re-suspended in 6 ml of complete RPMI-1640 medium, and incubated for 1 h at 37° C. in a $CO_2$ incubator. The cell fusion suspension was laid gently (100 µl per well) over mouse macrophages (feeder layer) contained in the 6×96-well plates. 24 h after the fusion, the HAT (hypoxanthine/aminopterin/thymidine) containing selection media (RPM)-1640) was added to the cells. The supernatants from the 96-well plates were tested by ELISA for antibody secretion. Confluent, positive clones by ELISA were amplified by transferring the cells into a 24-well plate containing a macrophage feeding layer plus 1×HAT. Positive clones underwent two rounds of sub-cloning by limiting dilution, and screened by ELISA for antibody secretion. Confluent, positive sub-clones by ELISA were amplified by transferring the cells into a 24-well plate containing a macrophage feeding layer plus 1×HAT. The final sub-clones were slowly adapted to medium without macrophages and HAT supplement. Finally, when adapted, the final hybridomas were established.

Production and Purification of Monoclonal Antibodies (mAbs)

Hybridoma cells are amplified in complete RPMI-1640 medium, washed twice in sterile PBS and resuspended at 100'000 cells per ml in Opti MEM I serum free medium (Gibco BRL, Life Technology, Basel, Switzerland). T175 flasks or Roller Bottles are inoculated with 100 ml and 800 ml cell suspension respectively. Cells are grown for 10-14 days. The supernatant is filtered and stored either at 4° C. or –20° C. with or without sodium azide. Purification is done using the Jumbosep™ (PALL Corp., East Hills, N.Y., USA) system. Hybridoma supernatants are washed extensively with sterile PBS and concentrated using spin columns.

Cells and Reagents

All cell lines were grown in RPMI, 10% FCS, except OCI-Ly7 grown in RPMI, 10% pooled human serum (Sigma Aldrich, Saint Louis, Mo., USA). The DLBCL cell lines established from patients SU-DHL 4, SU-DHL 6, SU-DHL 7 and OCI-Ly7 were provided by Dr A. Wiestner (Bethesda, Md., USA). L363 is a cell line established from a MM patient and provided by Dr Thomas Matthes (Geneva, Switzerland). HEK-293T cells were grown in DMEM, 10% FCS. Dendritic cells were obtained from peripheral monocytes treated with GMCSF/IL-4 as previously described (Huard, B. et al., Int Immunol 16, 467-75, 2004). Polymorphonuclear cells (PMN) and Peripheral Blood Leukocytes (PBL) were isolated from healthy donors. Blood was collected on sodium citrate (3.8%). Red blood cells were removed by sedimentation on PBS Dextran T500 (Amersham Biosciences, Otelfingen, Switzerland). Floating cells were separated by centrifugation on a layer of Ficoll-Paque (Amersham Biosciences). Pelleted cells were PMN, containing more that 95% of $CD15^+$ cells. Floating cells were PBL. To avoid PMN activation, all separation steps were performed at 4° C. in the presence of 5 µg/ml Polymixin B. Heparin (Liquemin, 5000 i.u./ml) was from Roche Pharma (Reinach, Switzerland). The following antibodies, anti-TACI (clone 1A1), anti-BCMA (clone Vickyl, rat IgG2a), anti-APRIL made in mouse against the extracellular portion (88-233) of APRIL (clones Aprily-1, -5, and -8, all IgG1), and polyclonal antibody ED (rabbit polyclonal antibody against the APRIL peptide GTG-GPSQNGEGYP, SEQ ID NO:1), also called Stalk-1, were obtained from Apotech Corp. (Epalinges, Switzerland). Recombinant APRIL (88-233) fused to ACRP30 (16-108), MegaAPRIL hereafter called acrpAPRIL and its control, headless ACRP30, hereafter called acrpCTRL, and BCMA (2-54)-Ig, were also from Apotech. Rabbit serum anti-syndecan 1, anti-syndecan 4 were from Santa-Cruz Biotechnology (Santa Cruz, Calif., USA). Anti-CD15 (clone C3D-1, IgM), anti-elastase (clone NP57, IgG1), and anti-CD20 (clone L26, IgG2a) were from DAKO (Zug, Switzerland).

Expression Constructs and Production

Expression vectors for Flag-ligands have been previously described (Holler, N. et al., Mol Cell Biol 23, 1428-40, 2003). $HuAPRIL_{A88}$ (88-233), $huAPRIL_{H98}$ (98-233) were produced in 293T cells in Opti MEM I serum free medium (Gibco BRL, Life Technology, Basel, Switzerland). Supernatants were concentrated 10-fold before use with centricon centrifugal filter devices (cut-off 10 kDa) (Millipore, Bedford, Mass., USA). Ligand concentration in Opti MEM supernatants was quantified by Western blot analysis with Aprily-1 as detection antibody and purified acrpAPRIL as standard.

Flow Cytometry

For antibody staining, cells were washed in PBS and incubated for 30 min at 4° C. with primary antibodies. Cells were washed once in PBS and incubated with secondary Alexa 488-conjugated goat anti mouse serum (Molecular Probes, Eugene, Oreg., USA) for an additional 30 min at 4° C. Cells were washed once in PBS before analysis using a FACSCAN and Cellquest (Becton Dickinson, San José, Calif., USA). Ligand staining was performed in a similar way, except that an anti-Flag, 5 µg/ml (IgG1, Clone M2, Sigma) was used as secondary reagent, and staining was revealed in an additional step with a phycoerythrin-conjugated goat-anti-mouse IgG1 (Jackson Immunoresearch, West Grove, Pa., USA). For total staining, cells were fixed/permeabilized with PBS, 1% formaldehyde, 1% saponin as previously described (Huard, B. & Karlsson, L., Nature 403, 325-8, 2000).

ELISA

For APRIL/proteoglycan interactions, microplates were coated over night at 4° C. with 1 µg/ml of purified heparan sulfate proteoglycan (Sigma). Plates were blocked with PBS, 0.05% $NaN_3$, 1% BSA, 5% sucrose for 1 h at room temperature (RT) and incubated with soluble APRIL diluted in PBS, BSA 0.1% for 4 h at RT. Detection was performed with Aprily-9 (1 µg/ml), followed by horse radish peroxidase (HRP) conjugated goat-anti mouse IgG serum (Jackson Immunoresearch). Tetramethylbenzidine (Sigma) was used as substrate for HRP. Two washes with PBS, 0.05% Tween 20 were performed between each step. For APRIL quantification in cell supernatants, microplates were coated over night at 4° C. with 1 µg/ml of BCMA-Ig. Plates were blocked as above before incubation with cell supernatant for 2 h. Standard was acrpAPRIL (Apotech). Detection was performed with Aprily-5 (1 µg/ml), washes and revelation were performed as above.

Gene Expression Analysis:

Total RNA (25 ng) prepared from cells using TRIzol Reagent (Gibco BRL, Life Technology, Basel, Switzerland) were reverse transcribed and amplified using a one-step RT-PCR kit (one step RT-PCR kit, Qiagen AG, Switzerland). All the primers used in this study spanned intronic sequences on the genomic DNA. For hTACI 5'-ctgggtacctgcatgtcctg-3' (SEQ ID NO:2) and 5'-agacttggccggactttgac-3' (SEQ ID NO:3), for hBCMA 5'-gggcagtgctcccaaaat-3' (SEQ ID NO:4) and 5'-tcgttttcgtggtgacaaga-3' (SEQ ID NO:5), and for hAPRIL, 5'-atgccagcctcatctcctttt-3' (SEQ ID NO:6) and 5'-tc-ctggattcggacaccata-3' (SEQ ID NO:7) were used as forward and reverse primers respectively. The control actin primers were forward 5'-ttaacgagaagctgtgctacgtc-3' (SEQ ID NO:8) and reverse 5'-atagtcctgcttgcttgctgatccac-3' (SEQ ID NO:9). Denaturation was performed at 94° C. for 1 min, annealing at 55° C. for 1 min and extension at 72° C. for 1 min. 40 cycles were applied for non-quantitative studies. Amplified mRNAs were visualized on agarose gels and ethidium bromide staining. Amplicon specificity was ascertained by restriction analysis with three selected enzymes for each primer pair.

Immunohistochemistry

The biopsy specimens were classified according to the Revised European-American Lymphoid (REAL) classification. Tissue micro arrays were constructed as described previously (Kononen, J. et al., Nat Med 4, 844-7, 1998). After carefully choosing a morphologically representative region on paraffin-embedded blocks (donor blocks), a core tissue biopsy of 1.6 mm was punched and transferred to a second paraffin-embedded block (receiver block). To overcome tumor heterogeneity and tissue loss, three core biopsies were performed from different areas of each tumor. After deparaffinization, sections were incubated for 10 min in methanol plus 0.6% hydrogen peroxide at RT, followed by washing with PBS solution. Slides were boiled in 0.01 M citrate buffer pH 6.0 for 3 min. Incubation with antibodies was carried out for 1 h at RT. For immunoperoxidase staining, secondary reagents were goat Ig anti-rabbit or anti-mouse IgG conjugated to HRP (Jackson Immunoresearch), followed by strept-ABComplex/HRP (Dako) and 3-amino-9-ethylcarbazole substrate (Sigma). For two color immunofluorescence stainings, isotype-specific goat anti-mouse sera conjugated to FITC or phycoerythrin (Jackson Immunoresearch) and goat Ig anti-rabbit IgG conjuguated to Alexa-488 (Molecular probes, Leiden, Netherlands) were used. Images were visualized under light or fluorescent microscopy with Axiophot 1 (Carl Zeiss AG, Oberkochen, Germany), captured with an axiocam (Carl Zeiss AG) color CCD camera, and treated on a Pentium III computer with axioVision™ software (Carl Zeiss AG). For cell staining, cells were injected into murine intestine. The injected intestine were fixed and embedded into paraffin. The resulting blocks were then treated as a standard tissue for immunostaining.

Patient Follow-Up and Statistical Analysis

All patients with a diagnosed DLBCL were seen and their specimen taken at the Geneva University Hospital and at the Basel University Hospital. Retrospective study of the clinical data from these patients was performed. The project was reviewed and approved by the Geneva University Hospital Ethics Committee. Stage, lactate dehydrogenase level, DLBCL sub-type and age were obtained by chart review. In situ APRIL expression at the date of biopsy was recorded as stated above. Survival was measured from the date of biopsy until the date of death from lymphoma. Co-morbidity led to patient exclusion. Patients alive at the last follow-up evaluation were censored (tickles on the curves). Kaplan-Meier overall survival curve was performed with the Prism software (Graphpad Software inc.). Comparison between groups was based on a log-rank statistical test.

---

The invention claimed is:

1. A monoclonal antibody Aprily-2 directed against soluble APRIL.

2. A hybridoma cell producing a monoclonal antibody Aprily-2 as deposited at the CNCM under the number I-3500.

3. A method of diagnosing an aggressive form of B cell lymphoma comprising:
   (i) measuring the amount of binding of monoclonal antibody Aprily-2 of claim 1 to a B cell lymphoma biopsy specimen; and
   (ii) measuring the amount of binding of a polyclonal or monoclonal antibody against the stalk fragment of APRIL to the B cell lymphoma biopsy specimen,
   wherein the amount of binding of the monoclonal antibody April-2 and of the polyclonal or monoclonal antibody against the stalk fragment of APRIL to said B cell lymphoma biopsy specimen indicates the presence of an aggressive form of B cell lymphoma.

4. The method of claim 3 wherein the antibody against the stalk fragment of APRIL is polyclonal antibody Stalk-1.

5. A kit comprising monoclonal antibody Aprily-2 of claim 1 and of a polyclonal or monoclonal antibody against the stalk fragment of APRIL.

6. The kit of claim 5 comprising polyclonal antibody Stalk-1 and monoclonal antibody Aprily-2.

* * * * *